United States Patent [19]
Wan et al.

[11] Patent Number: 5,837,529
[45] Date of Patent: Nov. 17, 1998

[54] METHOD FOR LYSING CELLS

[75] Inventors: Nick C. Wan, Newton; David S. McNeilly, Saugus; Charles William Christopher, Rockport, all of Mass.

[73] Assignee: Genzyme Corporation, Cambridge, Mass.

[21] Appl. No.: 632,203

[22] Filed: Apr. 15, 1996

Related U.S. Application Data

[63] Continuation of Ser. No. 324,455, Oct. 17, 1994, abandoned.
[51] Int. Cl.⁶ ..................................................... C12N 1/06
[52] U.S. Cl. ........................................ 435/259; 435/306.1
[58] Field of Search .................................. 435/259, 306.1

[56] References Cited

U.S. PATENT DOCUMENTS 4,296,204  10/1981  Grabner .
4,415,670  11/1983  Grabner .

FOREIGN PATENT DOCUMENTS 873653   7/1979  Belgium .
0308947  9/1987  European Pat. Off. .
2121022  4/1971  Germany .

*Primary Examiner*—Leon B. Lankford, Jr.
*Attorney, Agent, or Firm*—David G. Conlin; George W. Neuner

[57] ABSTRACT

This invention relates to a method for lysing cells. The method comprises simultaneously flowing a cell suspension and a lysis solution through a static mixer, wherein the cells exit the static mixer lysed. In another aspect of the present invention, the invention relates to a method for precipitating cell components, protein, and nucleic acids from a cell lysate or other solution containing precipitable material. The method comprises simultaneously flowing a cell lysate or other protein containing solution and a precipitating solution through a static mixer, wherein the lysate or protein solution exits the static mixer with its precipitable components precipitated. In another aspect of the present invention, the invention relates to a method where the two above-mentioned methods above are combined by using static mixers in series.

16 Claims, 3 Drawing Sheets

METHOD FOR LYSING CELLS

This application is a continuation of U.S. Ser. No. 08/324,455 filed Oct. 17, 1994, now abandoned.

BACKGROUND OF THE INVENTION

Increasing attention has been focused on the delivery of DNAs as therapeutic agents (i.e., DNA gene therapy) for the treatment of genetic diseases and for genetic immunization. Because of safety concerns with using potentially infectious viruses, researchers have been studying alternatives to viruses, using naked DNA or other non-viral methods of DNA delivery. One of the most promising non-viral methods in DNA therapy is the use of cationic lipids as delivery vehicles (Felgner, *Proc. Natl. Acad. Sci.,* 84:7413–7417, 1987). The cationic lipids adsorb to negatively charged DNA and facilitate entry of the DNA into target cells. Successful delivery of genes via lipids into airway epithelia of rodents (Hyde, *Nature,* 362:250–255, 1993) have been reported. If future 'gene therapy' proves to be effective, huge quantities of plasmids or appropriate DNA will be needed. However, current methods for isolating limited amounts of DNA may impede progress in this field.

Generally, the first step in making copies of a gene of interest starts with inserting the appropriate portion of DNA into plasmids which are then replicated in "host cells". Host cells include eukaryotic and prokaryotic cells. Once a sufficient amount of plasmids are produced in the host cells, the host cells are lysed to release the internally replicated plasmids.

Numerous mechanical methods for lysing cells have been developed and published. They include pressure, cavitation, sonic or ultrasonic waves, mechanical shaking with abrasives or grinding (Sadeva, *Biopharm* 7(2):26–36, 1994). However, few of these methods are suitable for recovery of DNA or other shear sensitive materials from cells. Chemical (Foster, *Biotechnol.* 10:273–277, 1992) and enzymatic (Andrews and Asenjo, *Tibtech.* 5:273–277, 1987) treatments, are more gentle and can be used for the recovery of shear sensitive products, such as DNA.

Generally, methods of plasmid isolation involve lysing the plasmid-containing cells with alkali (i.e. caustics) or enzymes in a test tube by gently inverting the tube several times. After the cells have been lysed, the cell lysate is mixed with a precipitating solution in a test tube by again gently inverting the test tube several times. The object is to precipitate contaminating cell components, e.g. genomic DNA, proteins, and protein-nucleic acid complexes, leaving the plasmids in solution. The plasmids can then be separated from the precipitate by centrifugation. While this approach can be used for small scale isolation, it is not practical for large scale production because the lysate is extremely viscous after the release of genomic DNA. Although, effective and gentle mixing of large quantities of viscous material can be achieved by using special agitators/mixers (e.g., planery mixers), these types of equipment are expensive and are not easily automated. In addition, the time of exposure of each plasmid to alkali in the large volume of solution is difficult to control and can vary a great deal and this may affect plasmid quality. Furthermore, it is crucial to handle the lysate very gently because any sheared genomic DNA may contaminate the sample and render later plasmid purification extremely difficult.

A need exists to develop an effective, economical, and automatable method for isolating high quality plasmids on a large scale to meet the future demand.

SUMMARY OF THE INVENTION

This invention relates to the use of static mixers in a novel manner, such as to rapidly lyse large amounts of cells. The lysis method comprises simultaneously flowing a cell suspension and a lysis solution through a static mixer, wherein the cells exit the static mixer lysed. A key advantage of the present invention is that multi-liter amounts of solution containing multi-gram amounts of cells can be lysed rapidly, making large scale biological procedures involving cell lysis feasible.

In another aspect of the present invention, the invention relates to a rapid method for precipitating cell components, protein, and nucleic acids from a cell lysate or other solution to be precipitated, using a static mixer. The method comprises simultaneously flowing a cell lysate or other protein-containing solution and a precipitating solution through a static mixer, wherein the lysate or protein solution exits the static mixer with its precipitable components precipitated.

In another aspect of the present invention, the invention relates to a method where the two above-mentioned methods are combined by using static mixers in series, i.e., by first lysing the cells through a first static mixer and then precipitating the cell lysate through a second static mixer.

In another aspect of the present invention, the invention relates to a method for releasing intact usable plasmids from plasmid-containing cells, comprising simultaneously flowing a solution containing the plasmid-containing cells and a lysate solution through a static mixer wherein the plasmid-containing cells exit the static mixer lysed and the plasmids released. In addition, the method of releasing a plasmid further includes a preliminary step, prior to the lysing step, of simultaneously diluting the cells to be lysed to an optimal cell density by flowing the plasmid-containing cell suspension and a solution through a static mixer prior to simultaneously flowing the diluted cell suspension with a lysis solution through another static mixer (i.e., a second static mixer) with the same results. Furthermore, this method can include the precipitation step, explained above, where the cell lysate of the second static mixer is combined with a precipitating solution through a third static mixer.

DETAILED DESCRIPTION OF THE INVENTION

Figure 1:
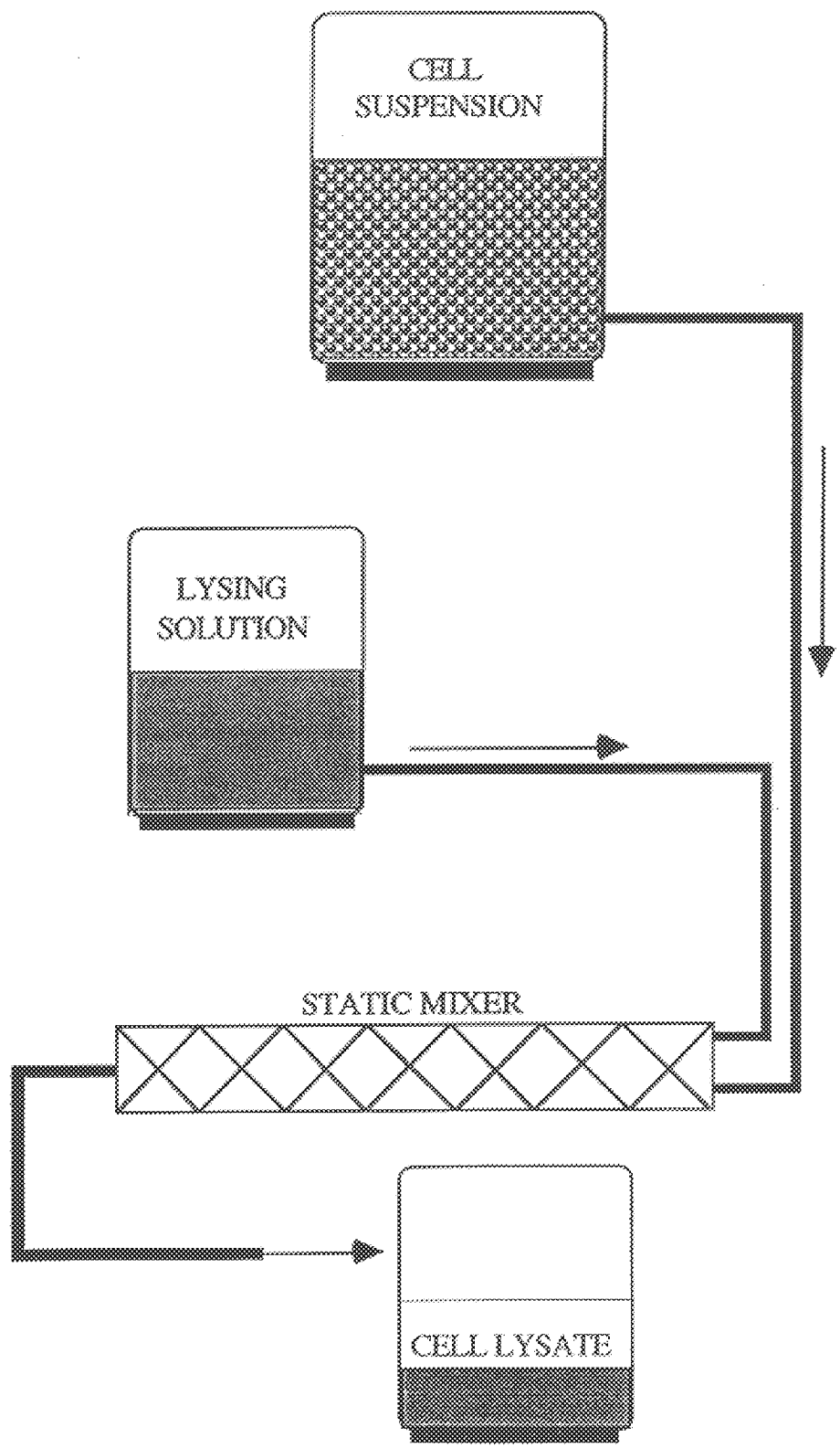
FIG. 1 is an illustration of the method of the present invention where cells are passed through a static mixer simultaneously with a lysis solution, the result being that the cells exit the static mixer lysed.
Figure 2:
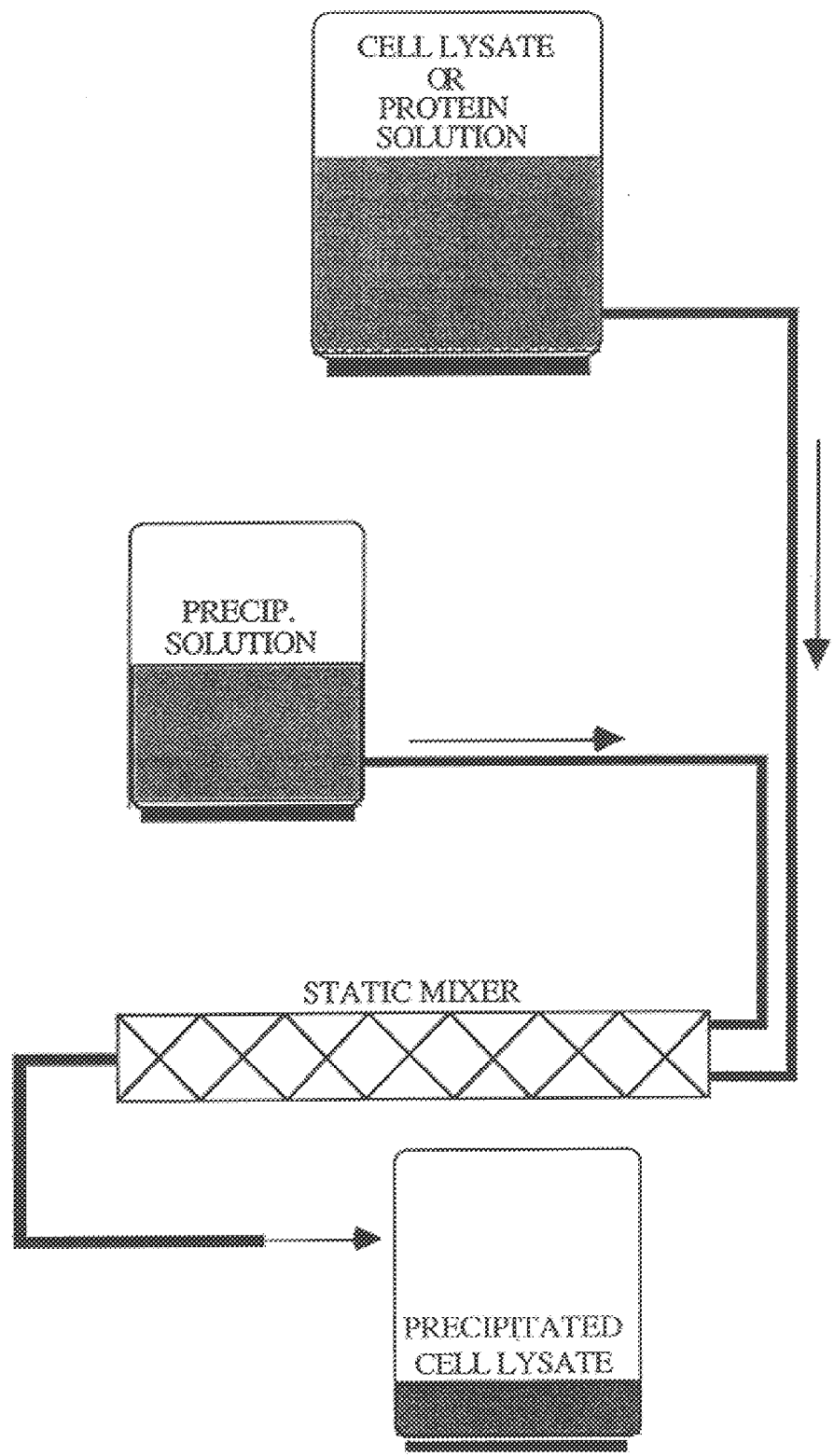
FIG. 2 is an illustration of the method of the present invention where a cell lysate (or protein solution) is passed through a static mixer simultaneously with a precipitating solution the result being that the cell lysate (or protein solution) exits the static mixer precipitated.

This invention is based upon the discovery that static mixers could be used to lyse cells containing plasmids, releasing the plasmids from the cells. The advantage of using such a device is that large volumes of cells can be gently and continuously lysed in-line using the static mixer and that other static mixers could be placed in-line to accomplish other functions such as dilution and precipitation. This method greatly simplifies the process of isolating plasmids from large volumes of material such that plasmid DNA is not damaged by the process. Previous methods of plasmid isolation involving caustic lysing and precipitation, which involved expensive and specialized equipment, were not practical for large scale plasmid purification. The method of the present invention can be used to lyse any type of cell (i.e., prokaryotic or eukaryotic) for any purpose related to lysing, such as releasing desired nucleic acids or proteins from target cells to be subsequently purified. In a preferred embodiment, the method of the present invention is used to lyse host cells containing plasmids to release plasmids.

The term "lysing" refers to the action of rupturing the cell wall and/or cell membrane of a cell which is in a buffered solution (i.e., cell suspension) through chemical treatment using a solution containing a lysing agent. Lysing agents include for example, alkali, detergents, organic solvents, and enzymes. In a preferred embodiment, the lysis of cells is done to release intact plasmids from host cells. For purposes of the present invention the term "simultaneously" referring to the passage of substances through a static mixer, means that the subject substances are passing through the static mixer at approximately the same time. For purposes of the present invention the term "flowing" refers to the passing of a liquid at a particular flow rate (e.g., liters per minute) through the static mixer, usually by the action of a pump. It should be noted that the flow rate through the static mixer is believed to affect the efficiency of lysis, precipitation and mixing. Suitable static mixers useful in the method of the present invention include any flow through device referred to in the art as a static or motionless mixer of a length sufficient to allow the processes of the present invention. For example, for the purpose of lysing cells, the static mixer would need to have a length which would provide enough contact time between the lysing solution and the cells to cause the lysis of the subject cells during passage through the mixer. In a preferred embodiment, suitable static mixers contain an internal helical structure which causes two liquids to come in contact with one another in an opposing rotational flow causing the liquids to mix together in a turbulent flow.

For purposes of the present invention the term "precipitating" refers to the action of precipitating proteins and other cell components from a solution through chemical precipitation using a solution containing a precipitating agent. Precipitating agents include sodium dodecyl sulfate (SDS) and potassium acetate.

The term "plasmid" for purposes of the present invention include any type of replication vector which has the capability of having a non-endogenous DNA fragment inserted into it. Procedures for the construction of plasmids include those described in Maniatis et al., *Molecular Cloning, A Laboratory Manual,* 2d, Cold Spring Harbor Laboratory Press (1989).

Figure 3:
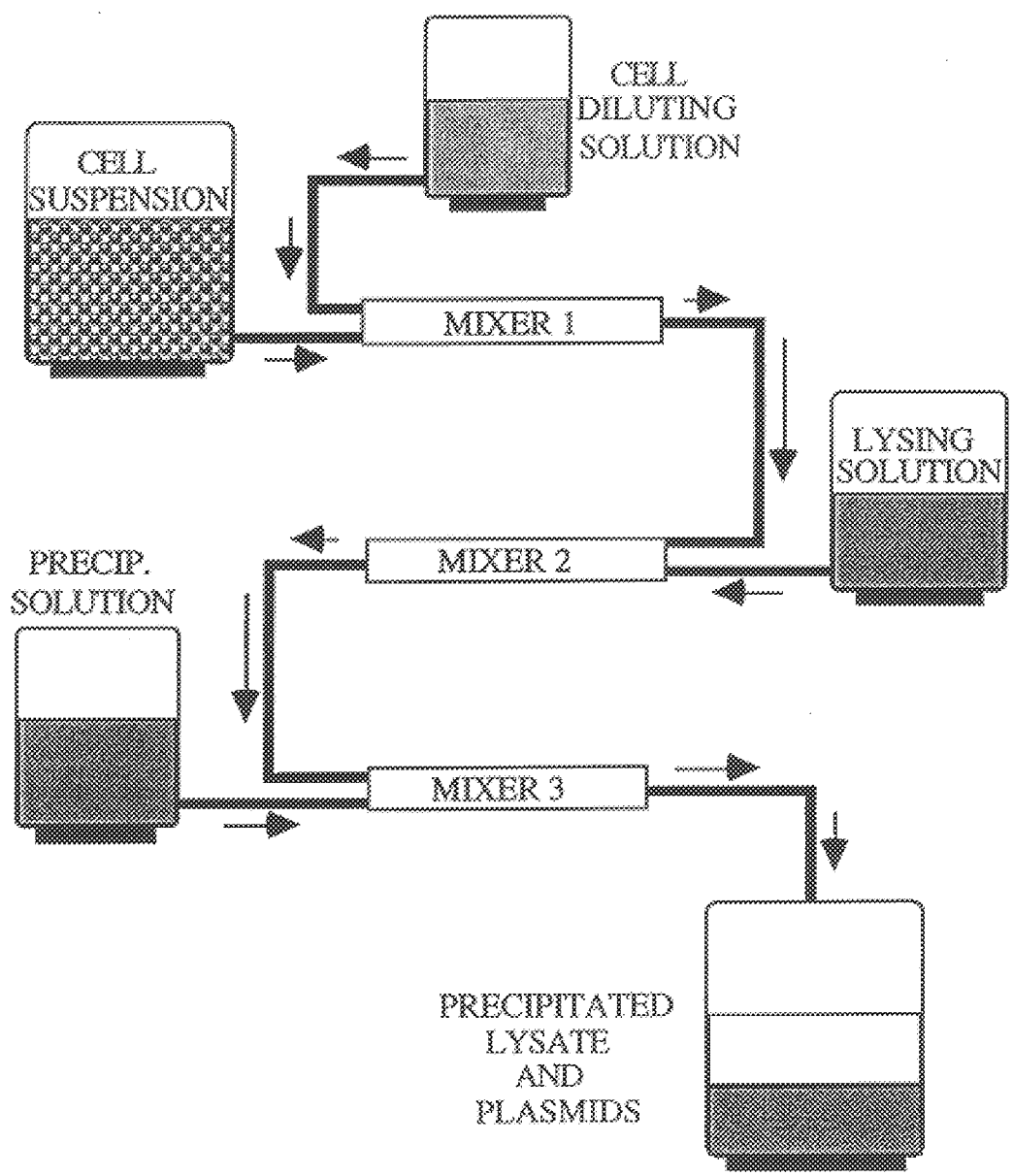
FIG. 3 is an illustration of the method of the present invention where cells are first passed through a static mixer simultaneously with a cell diluting solution, then the mixture exiting the first static mixer is passed through a second static mixer along with a lysis solution, then that mixture is passed through a third static mixer simultaneously with a precipitating solution.

In a preferred embodiment, illustrated in FIG. 3, the method of releasing plasmids from plasmid-containing host cells, comprises first simultaneously flowing the media containing the plasmid-containing host cells with a buffered solution through a static mixer i.e., the first static mixer. The mixture that exits the first static mixer is thereby equilibrated with the buffer. The buffered mixture is then simultaneously flow ed through a second static mixer along with a lysis solution which, while passing through the length of the static mixer, lyses the cells releasing the plasmid and cellular components. The cell lysate is then passed through a third static mixer along with a precipitation buffer which precipitates most of the cellular components but not the plasmids.

EXEMPLIFICATION

*Escherichia coli* (*E. coli*) cells that had been grown in a nutrient medium to a high cell density, the culture was then diluted directly by flowing the cells through a ½"×27", 32-element, Kenics static mixer ( purchased from Chemineer, N. Andover, Mass.) along with a resuspending solution (50 mM Tris/HCl, 10 mM EDTA, 100 mg RNaseA/ml, pH 8.0) until the exiting cells had an optical density of 25–40 at 600 nm, as read by a spectrophotometer. The diluted cell suspension exiting the first static mixture was then flowed through a second static mixer (same type of mixer as above) along with a lysis solution (200 mM NaOH, 1% weight/volume SDS, ) at a rate of 100–1,300 ml/min. The cells exited the second static mixer lysed (i.e., cell lysate). The cell lysate exiting the second static mixer was then flowed through a third static mixer (same type as above) with a precipitating solution (2.6M potassium acetate, pH 5.2) at a similar flow rate as passed through the second static mixer. The exiting suspension contained precipitated *E. coli* genomic DNA, proteins, and insoluble debris and the soluble plasmids. About 45 liters of mixture was collected from the third static mixer and processed. Approximately 1 gram of plasmid was isolated from this run.

All of the static mixers above were connected in series by tubing and the respective solutions were flowed or pumped though the static mixers by peristaltic pumps (Cole-Parmer, Chicago, Ill.).

Equivalents

Those skilled in the art will recognize, or be able to ascertain, using no more than routine experimentation, many equivalents to the specific embodiments of the invention described herein. Such equivalents are intended to be encompassed by the following claims:

The invention claimed is:

1. A method of lysing cells while avoiding shearing genomic DNA, said method comprising:

providing a static mixer having no moving parts;

providing a quantity of fluid containing a cell suspension;

flowing the fluid containing the cell suspension through the mixer until the entire quantity of cell suspension has passed through the mixer;

simultaneously flowing a lysis solution through the static mixer at a flow rate which allows sufficient contact of the cells and the lysis solution to provide for lysis of the cells, wherein the fluid that exits the static mixer contains lysed cells.

2. The method of claim 1 wherein the lysis solution is a solution containing a lysis agent selected from the group consisting of an alkali, a detergent, an organic solvent, and an enzyme or a mixture thereof.

3. The method of claim 1 wherein the cells are plasmid-containing cells.

4. A method of precipitating cellular components from plasmids in a solution of cell lysate, said method comprising:

providing a static mixer having no moving parts;

providing a quantity of solution of cell lysate containing cellular components including plasmids;

flowing the cell lysate solution through the mixer until the entire quantity of cell suspension has passed through the mixer;

simultaneously flowing a precipitating solution through the static mixer at a flow rate which allows sufficient contact of the cellular components and the precipitating solution to provide for precipitation of the cellular components leaving the plasmids in solutions, wherein the solution that exits the static mixer contains soluble plasmids and precipitated cellular components.

5. The method of claim 4 wherein the precipitating solution is a solution containing a precipitating agent selected from the group consisting of sodium dodecyl sulfate and potassium acetate or a mixture thereof.

6. The method of claim 4 wherein the cell lysate contains plasmids.

7. A method of releasing plasmids from plasmid-containing cells while avoiding shearing genomic DNA, said method comprising:

providing a static mixer having no moving parts;

providing a quantity of plasmid-containing cells in a fluid suspension;

flowing the fluid suspension through the mixer until the entire quantity of plasmid-containing cells has passed through the mixer;

simultaneously flowing a lysis solution through the static mixer at a flow rate which allows sufficient contact of the cells and the lysis solution to provide for lysis of the cells, p1 wherein the fluid that exits the static mixer contains soluble plasmids released from the lysed cells.

8. The method of claim 7 wherein the lysis solution is a solution containing a lysis agent selected from the group consisting of an alkali, a detergent, an organic solvent, and an enzyme or mixture thereof.

9. A method of releasing plasmids from plasmid-containing cells while avoiding shearing genomic DNA, said method comprising:

providing a first static mixer having no moving parts;

providing a quantity of plasmid-containing cells in a fluid suspension;

flowing the fluid suspension through the mixer until the entire quantity of plasmid-containing cells has passed through the mixer;

simultaneously flowing a buffer solution through the static mixer at a flow rate to provide a fluid exiting the first static mixer containing a mixture of the suspension of plasmid-containing cells in the buffer solution;

providing a second static mixer having no moving parts;

flowing the mixture from the first static mixer into the second static mixer;

simultaneously flowing a lysis solution through the second static mixer at a flow rate which allows sufficient contact of the cells and the lysis solution to provide for lysis of the cells, wherein the fluid that exits the second static mixer contains soluble plasmids released from the lysed cells.

10. The method of claim 9 wherein the lysis solution is a solution containing a lysis agent selected from the group consisting of an alkali, a detergent, an organic solvent, and an enzyme or mixture thereof.

11. A method of separating plasmids from plasmid-containing cells while avoiding shearing genomic DNA, said method comprising:

providing a first static mixer having no moving parts;

providing a quantity of plasmid-containing cells in a fluid suspension;

flowing the fluid suspension through the first static mixer until the entire quantity of plasmid-containing cells has passed through the mixer;

simultaneously flowing a buffer solution through the first static mixer at a flow rate to provide a fluid exiting the first static mixer containing a mixture of the suspension of plasmid-containing cells in the buffer solution;

providing a second static mixer having no moving parts;

flowing the mixture from the first static mixer into the second static mixer until it has passed entirely through it;

simultaneously flowing a lysis solution through the second static mixer at a flow rate which allows sufficient contact of the cells and the lysis solution to provide for lysis of the cells, wherein the fluid that exits the second static mixer contains plasmids and other cellular components released from the lysed cells;

providing a third static mixer having no moving parts;

flowing the mixture from the second static mixer into the third static mixer until the entire mixture has passed through;

simultaneously flowing a precipitating solution through the third static mixer at a flow rate which allows sufficient contact of the cellular components and the precipitating solution to provide for precipitation of the cellular components leaving the plasmids in solutions, wherein the fluid that exits the third static mixer contains soluble plasmids and precipitated cellular components.

12. The method of claim 11 wherein the lysis solution is a solution containing a lysis agent selected from the group consisting of an alkali, a detergent, an organic solvent, and an enzyme or mixture thereof.

13. The method of claim 11 wherein the precipitating solution is a solution containing a precipitating agent selected from the group consisting of sodium dodecyl sulfate and potassium acetate or mixture thereof.

14. A method of separating plasmids from plasmid-containing cells while avoiding shearing genomic DNA, said method comprising:

providing a first static mixer having no moving parts;

providing a quantity of plasmid-containing cells in a fluid suspension;

flowing the fluid suspension through the first static mixer until the entire quantity of plasmid-containing cells has passed through the mixer;

simultaneously flowing a lysis solution through the first static mixer at a flow rate which allows sufficient contact of the cells and the lysis solution to provide for lysis of the cells, wherein the fluid that exits the first static mixer contains plasmids and other cellular components released from the lysed cells;

providing a second static mixer having no moving parts;

flowing the fluid from the first static mixer into the second static mixer until it has passed entirely through it;

simultaneously flowing a precipitating solution through the second static mixer at a flow rate which allows sufficient contact of the cellular components and the precipitating solution to provide for precipitation of the cellular components leaving the plasmids in solutions, wherein the fluid that exits the second static mixer contains soluble plasmids and precipitated cellular components.

15. The method of claim 14 wherein the lysis solution is a solution containing a lysis agent selected from the group consisting of an alkali, a detergent, an organic solvent, and an enzyme or mixture thereof.

16. The method of claim 14 wherein the precipitating solution is a solution containing a precipitating agent selected from the group consisting of sodium dodecyl sulfate and potassium acetate or mixture thereof.

* * * * *